(12) United States Patent
Klanner et al.

(10) Patent No.: US 8,088,962 B2
(45) Date of Patent: Jan. 3, 2012

(54) METHOD FOR PRODUCING BUTADIENE FROM N-BUTANE

(75) Inventors: Catharina Klanner, Mannheim (DE); Götz-Peter Schindler, Mannheim (DE); Sven Crone, Limburgerhof (DE); Frieder Borgmeier, Mannheim (DE); Mark Duda, Ludwigshafen (DE); Falk Simon, Bensheim (DE)

(73) Assignee: BASF SE, Ludwigshafen (DE)

( * ) Notice: Subject to any disclaimer, the term of this patent is extended or adjusted under 35 U.S.C. 154(b) by 1204 days.

(21) Appl. No.: 11/813,935

(22) PCT Filed: Jan. 16, 2006

(86) PCT No.: PCT/EP2006/050217
§ 371 (c)(1),
(2), (4) Date: Jul. 13, 2007

(87) PCT Pub. No.: WO2006/075025
PCT Pub. Date: Jul. 20, 2006

(65) Prior Publication Data
US 2008/0183024 A1    Jul. 31, 2008

(30) Foreign Application Priority Data
Jan. 17, 2005  (DE) .......... 10 2005 002 127

(51) Int. Cl.
*C07C 5/333* (2006.01)

(52) U.S. Cl. ......... 585/325; 585/616; 585/621; 585/628

(58) Field of Classification Search .......... 585/325, 585/616, 621, 628
See application file for complete search history.

(56) References Cited

U.S. PATENT DOCUMENTS
2005/0171311 A1   8/2005   Schindler et al.

FOREIGN PATENT DOCUMENTS
| | | |
|---|---|---|
| DE | 1543152 | 7/1969 |
| GB | 1107432 | 3/1968 |
| WO | 2004/007408 | 1/2004 |

*Primary Examiner* — Thuan Dinh Dang
(74) *Attorney, Agent, or Firm* — Connolly Bove Lodge & Hutz LLP

(57) ABSTRACT

A process for preparing butadiene, comprising A) providing a stream (a) comprising n-butane; B) feeding stream (a) comprising into at least one first dehydrogenation zone and non-oxidatively catalytically dehydrogenating n-butane to obtain a stream (b) comprising n-butane, 1-butene, 2-butene, butadiene, hydrogen and low-boiling secondary constituents; C) feeding stream (b) and an oxygenous gas into at least one second dehydrogenation zone and oxidatively dehydrogenating n-butane, 1-butene and 2-butene to obtain a stream (c) comprising n-butane, 2-butene, butadiene, low-boiling secondary constituents, carbon oxides and steam, wherein stream (c) has a higher content of butadiene than stream (b); D) removing the low-boiling secondary constituents and steam to obtain a stream (d) substantially consisting of n-butane, 2-butene and butadiene; E) separating stream (d) into a stream (e1) consisting substantially of n-butane and 2-butene and a stream (e2) consisting substantially of butadiene by extractive distillation; F) recycling stream (e1) into the first dehydrogenation zone.

7 Claims, 1 Drawing Sheet

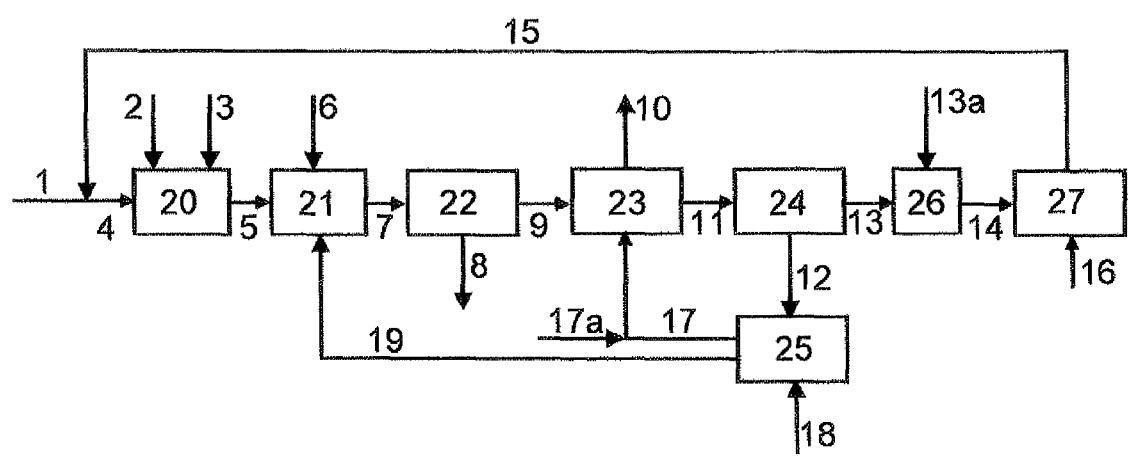

METHOD FOR PRODUCING BUTADIENE FROM N-BUTANE

RELATED APPLICATIONS

This application is a national stage application (under 35 U.S.C. §371) of PCT/EP2006/050217 filed Jan. 16, 2006, which claims benefit of German application 10 2005 002 127.1 filed Jan. 17, 2005.

Butadiene is an important basic chemical and is used, for example, to produce synthetic rubbers (butadiene homopolymers, styrene-butadiene rubber or nitrile rubber) or for preparing thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Dimerization of butadiene also allows vinylcyclohexene to be obtained, which can be dehydrogenated to styrene.

Butadiene may be prepared by thermal cracking (steamcracking) of saturated hydrocarbons, in which case the raw starting material used is typically naphtha. In the steamcracking of naphtha, a hydrocarbon mixture of methane, ethane, ethene, acetylene, propane, propene, propyne, allene, butenes, butadiene, butynes, methylallene, $C_5$ and higher hydrocarbons is obtained.

A disadvantage of obtaining butadiene in the cracking process is that relatively large amounts of undesired coproducts are inevitably obtained.

It is an object of the invention to provide a process for preparing butadiene from n-butane, in which coproducts are obtained to a minimal extent.

The object is achieved by a process for preparing butadiene from n-butane, comprising the steps of
A) providing a feed gas stream a comprising n-butane;
B) feeding the feed gas stream a comprising n-butane into at least one first dehydrogenation zone and nonoxidatively catalytically dehydrogenating n-butane to obtain a product gas stream b comprising n-butane, 1-butene, 2-butene, butadiene, hydrogen and low-boiling secondary constituents, with or without carbon oxides and with or without steam;
C) feeding the product gas stream b of the nonoxidative catalytic dehydrogenation and an oxygenous gas into at least one second dehydrogenation zone and oxidatively dehydrogenating n-butane, 1-butene and 2-butene to obtain a product gas stream c comprising n-butane, 2-butene, butadiene, low-boiling secondary constituents, carbon oxides and steam, said product gas stream c having a higher content of butadiene than product gas stream b;
D) removing the low-boiling secondary constituents and steam to obtain a $C_4$ product gas stream d substantially consisting of n-butane, 2-butene and butadiene;
E) separating the $C_4$ product gas stream d into a stream e1 consisting substantially of n-butane and 2-butene and a product-of-value stream e2 consisting substantially of butadiene by extractive distillation;
F) recycling stream e1 into the first dehydrogenation zone.

The process according to the invention features particularly effective utilization of the raw materials. Thus, losses of the n-butane raw material are minimized by recycling unconverted n-butane into the dehydrogenation. As a result of the coupling of nonoxidative catalytic dehydrogenation and oxidative dehydrogenation, a high butadiene yield is achieved.

In a first process part, A, a feed gas stream a comprising n-butane is provided. Typically, the starting raw materials are n-butane-rich gas mixtures such as liquefied petroleum gas (LPG). LPG comprises substantially saturated $C_2$-$C_5$ hydrocarbons. In addition, it also comprises methane and traces of $C_6^+$ hydrocarbons. The composition of LPG may vary greatly. Advantageously, the LPG used comprises at least 10% by weight of butanes.

Alternatively, a refined $C_4$ stream from crackers or refineries may be used.

The n-butane-containing dehydrogenation feed gas stream is generally crude butane. It will preferably be crude butane which fulfills the specifications listed below (analogously to DE 102 45 585, data in parts by volume):

content of n-butane $\geq 90\%$ by volume, usually $\geq 93\%$ by volume, generally $\geq 95\%$ by volume;
content of isobutane $\leq 1\%$ by volume, usually $\leq 0.5\%$ by volume, generally $\leq 0.3\%$ by volume;
content of 1-butene $\leq 1\%$ by volume, usually $\leq 0.5\%$ by volume, generally $\leq 0.3\%$ by volume;
content of cis-butene $\leq 1\%$ by volume, usually $\leq 0.5\%$ by volume, generally $\leq 0.3\%$ by volume;
content of trans-butene $\leq 1\%$ by volume, usually $\leq 0.5\%$ by volume, generally $\leq 0.3\%$ by volume;
content of isobutene $\leq 1\%$ by volume, usually $\leq 0.5\%$ by volume, generally $\leq 0.3\%$ by volume;
Total content of $C_4$ hydrocarbons other than butanes and butenes $\leq 1\%$ by volume, usually $\leq 0.5\%$ by volume, generally $\leq 0.3\%$ by volume;
content of methane $\leq 10$ ppm, usually $\leq 5$ ppm, generally from 0 to 1 ppm;
content of propane $\leq 100$ ppm, usually $\leq 90$ ppm, generally from 50 to 80 ppm;
total content of $C_5$ hydrocarbons $\leq 5\%$ by volume;
total content of $C_6$ hydrocarbons $\leq 5\%$ by volume;
total content of $C_7$-$C_8$ hydrocarbons $\leq 20$ ppm;
total content of oxygen-containing organic compounds $\leq 30$ ppm;
content of ionogenic Cl $\leq 0.1$ mg/kg;
total content of Cl-containing compounds and expressed as Cl $\leq 0.1$ mg/kg;
total content of F-containing compounds and expressed as F $\leq 0.1$ mg/kg;
total content of S-containing compounds and expressed as S $\leq 0.1$ mg/kg;
Ag$\leq 1$ µg/kg, Al$\leq 4$ µg/kg, As$\leq 1$ µg/kg, Au$\leq 1$ µg/kg, Ba$\leq 10$ µg/kg, Be$\leq 1$ µg/kg, Bi$\leq 1$ µg/kg, Ca$\leq 4$ µg/kg, Cd$\leq 1$ µg/kg, Co$\leq 1$ µg/kg, Cr$\leq 1$ µg/kg, Cu$\leq 0.2$ mg/kg, Fe$\leq 30$ µg/kg, Ga$\leq 1$ µg/kg, Ge$\leq 2$ µg/kg, Hg$\leq 1$ µg/l, In$\leq 1$ µg/kg, Ir$\leq 1$ µg/kg, K$\leq 3$ µg/kg, Li$\leq 1$ µg/kg, Mg$\leq 1$ µg/kg, Mn$\leq 2$ µg/kg, Mo$\leq 1$ µg/kg, Na$\leq 4$ µg/kg, Nb$\leq 1$ µg/kg, Ni$\leq 3$ µg/kg, Pb$\leq 10$ µg/kg, Pd$\leq 1$ µg/kg, Pt$\leq 1$ µg/kg, Rh$\leq 1$ µg/kg, Sb$\leq 1$ µg/kg, Sn$\leq 1$ µg/kg, Sr$\leq 1$ µg/kg, Ta$\leq 1$ µg/kg, Ti$\leq 1$ µg/kg, Tl $\leq 1$ µg/kg, V$\leq 1$ µg/kg, Zn$\leq 0.1$ mg/kg, Zr$\leq 1$ µg/kg.

In one variant of the process according to the invention, the provision of the dehydrogenation feed gas stream comprising n-butane comprises the steps of
(A1) providing a liquefied petroleum gas (LPG) stream,
(A2) removing propane and any methane, ethane and $C_5^+$ hydrocarbons (mainly pentanes, additionally hexanes, heptanes, benzene, toluene) from the LPG stream to obtain a stream comprising butanes (n-butane and isobutane),
(A3) removing isobutane from the stream comprising butanes to obtain the feed gas stream comprising n-butane, and, if appropriate, isomerizing the isobutane removed to give an n-butane/isobutane mixture and recycling the n-butane/isobutane mixture into the isobutane removal.

Propane and any methane, ethane and $C_5^+$ hydrocarbons are removed, for example, in one or more customary rectification columns. For example, in a first column, low boilers (methane, ethane, propane) may be removed overhead and, in a second column, high boilers ($C_5^+$ hydrocarbons) may be removed at the bottom of the column. A stream comprising butanes (n-butane and isobutane) is obtained, from which isobutane is removed, for example in a customary rectification column. The remaining stream comprising n-butane is used as the feed gas stream for the downstream butane dehydrogenation.

The isobutane stream removed is preferably subjected to isomerization. To this end, the stream comprising isobutane is fed into an isomerization reactor. The isomerization of isobutane to n-butane may be carried out as described in GB-A 2 018 815. An n-butane/isobutane mixture is obtained and is fed into the n-butane/isobutane separating column.

The isobutane stream removed may also be sent to a further use, for example for preparing methacrylic acid, polyisobutene or methyl tert-butyl ether.

In one process part, B, the feed gas stream comprising n-butane is fed into a dehydrogenation zone and subjected to a nonoxidative catalytic dehydrogenation. In this dehydrogenation, n-butane is partly dehydrogenated in a dehydrogenation reactor over a dehydrogenating catalyst to give 1-butene and 2-butene, and butadiene is also formed. In addition, hydrogen and small amounts of methane, ethane, ethene, propane and propene are obtained. Depending on the method of the dehydrogenation, carbon oxides (CO, $CO_2$), water and nitrogen may also be present in the product gas mixture of the nonoxidative catalytic n-butane dehydrogenation. Unconverted n-butane is additionally present in the product gas mixture.

The nonoxidative catalytic n-butane dehydrogenation may be carried out with or without oxygenous gas as a cofeed.

One feature of the nonoxidative method compared to an oxidative method is the presence of hydrogen in the effluent gas. In the oxidative dehydrogenation, free hydrogen is not formed in substantial amounts.

The nonoxidative catalytic n-butane dehydrogenation may in principle be carried out in any reactor types and methods disclosed by the prior art. A comparatively comprehensive description of dehydrogenation processes suitable in accordance with the invention is also contained in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

A suitable reactor form is a fixed bed tubular or tube bundle reactor. In these reactors, the catalyst (dehydrogenation catalyst and, when working with oxygen as the cofeed, a specialized oxidation catalyst if appropriate) is disposed as a fixed bed in a reaction tube or in a bundle of reaction tubes. The reaction tubes are customarily heated indirectly by the combustion of a gas, for example a hydrocarbon such as methane, in the space surrounding the reaction tubes. It is favorable to apply this indirect form of heating only to about the first 20 to 30% of the length of the fixed bed and to heat the remaining bed length to the required reaction temperature by the radiant heat released in the course of indirect heating. Customary reaction tube internal diameters are from about 10 to 15 cm. A typical dehydrogenation tube bundle reactor comprises from about 300 to 1000 reaction tubes. The internal temperature in the reaction tubes typically varies in the range from 300 to 700° C., preferably in the range from 400 to 700° C. The working pressure is customarily from 0.5 to 8 bar, frequently from 1 to 2 bar, when a small steam dilution is used (similar to the Linde process for propane dehydrogenation), or else from 3 to 8 bar when using a high steam dilution (similar to the steam active reforming process (STAR process) for dehydrogenating propane or butane of Phillips Petroleum Co., see U.S. Pat. No. 4,902,849, U.S. Pat. No. 4,996,387 and U.S. Pat. No. 5,389,342). Typical catalyst hourly space velocities (GHSV) are from 500 to 2000 $h^{-1}$, based on the hydrocarbon used. The catalyst geometry may, for example, be spherical or cylindrical (hollow or solid).

On the industrial scale, a plurality of (for example three) such tube bundle reactors may be operated in parallel in the $1^{st}$ dehydrogenation zone. It is possible in accordance with the invention, if appropriate, for one (or two) of these reactors to be in dehydrogenating operation, while the catalyst charge is being regenerated in a second (third) reactor, without the operation in the $2^{nd}$ dehydrogenation zone having to be shut down. Such a procedure is appropriate, for example, in the BASF-Linde propane dehydrogenation process described in the literature.

Such a procedure can also be employed in what is known as the "steam active reforming (STAR) process" which has been developed by Phillips Petroleum Co. (cf., for example, U.S. Pat. No. 4,902,849, U.S. Pat. No. 4,996,387 and U.S. Pat. No. 5,389,342). The dehydrogenation catalyst used in the STAR process is preferably platinum, comprising promoters, on zinc (-magnesium) spinel as a support (cf., for example, U.S. Pat. No. 5,073,662). In contrast to the BASF-Linde propane dehydrogenation process, the propane to be dehydrogenated is diluted with steam in the STAR process. A typical molar ratio of steam to propane is in the range from 4 to 6. The starting reactor pressure is frequently from 3 to 8 bar and the reaction temperature is appropriately from 480 to 620° C. Typical catalyst hourly space velocities of propane are from 200 to 4000 $h^{-1}$ (GHSV).

The heterogeneously catalyzed, nonoxidative n-butane dehydrogenation in the process according to the invention may also be carried out in a moving bed. For example, the moving catalyst bed may be accommodated in a radial flow reactor. In this reactor, the catalyst moves slowly from top to bottom, while the reaction gas mixture flows radially. This procedure is employed, for example, in what is known as the UOP-Oleflex dehydrogenation process. Since the reactors in this process are operated quasi-adiabatically, it is appropriate to operate a plurality of reactors connected in series as a battery (typically up to four). Within the battery, a recycle stream comprising n-butane from the $2^{nd}$ dehydrogenation zone may be fed in. This allows excessively great temperature differences of the reaction gas mixture at the reactor inlet and at the reactor outlet to be prevented and good overall yields nevertheless to be achieved.

When the catalyst bed has left the moving bed reactor, it is sent to regeneration and subsequently reused. The dehydrogenation catalyst used for this process may, for example, be a spherical dehydrogenation catalyst which consists substantially of platinum on spherical alumina support. In the UOP variant, hydrogen is added to the propane to be dehydrogenated in order to prevent premature catalyst aging. The working pressure is typically from 2 to 5 bar. The molar hydrogen to propane ratio is typically from 0.1 to 1. The reaction temperatures are preferably from 550 to 650° C. and the residence time of the catalyst in one reactor is from about 2 to 10 h.

In the fixed bed process described, the catalyst geometry may likewise be spherical, but also cylindrical (hollow or solid) or be configured geometrically in a different way.

The nonoxidative catalytic n-butane dehydrogenation may also be carried out under heterogeneous catalysis in a fluidized bed, as described in Chem. Eng. Sci. 1992 b, 47 (9-11) 2313. Appropriately, two fluidized beds are operated in parallel, of which one is generally in the state of regeneration. The working pressure is typically from 1 to 2 bar, the dehydrogenation temperature generally from 550 to 600° C. The heat required for the dehydrogenation is introduced into the reaction system by preheating the dehydrogenation catalyst to the reaction temperature. The admixing of a cofeed comprising oxygen allows the preheater to be dispensed with, and the heat required to be generated directly in the reactor system by combustion of hydrogen and/or hydrocarbons in the presence of oxygen. If appropriate, a cofeed comprising hydrogen may additionally be admixed.

The heterogeneously catalyzed n-butane dehydrogenation in a fluidized bed may also be carried out as described for propane in proceedings De Witt, Petrochem. Review, Houston, Tex., 1992 a, N1. Alternatively to the above-described procedures, the heterogeneously catalyzed n-butane hydrogenation may also be realised analogously to the process developed by ABB Lummus Crest (cf. proceedings De Witt, Petrochem. Review, Houston, Tex., 1992, P1).

The nonoxidative catalytic n-butane dehydrogenation may be carried out in a tray reactor with or without oxygenous gas as a cofeed. This reactor comprises one or more successive catalyst beds. The number of catalyst beds may be from 1 to 20, advantageously from 1 to 6, preferably from 1 to 4 and in particular from 1 to 3. The catalyst beds are preferably flowed through radially or axially by the reaction gas. In general, such a tray reactor is operated with a fixed catalyst bed. In the simplest case, the fixed catalyst beds in a shaft furnace reactor are arranged axially or in the annular gaps of concentric cylindrical grids. One shaft furnace reactor corresponds to one tray. The performance of the dehydrogenation in a single shaft furnace reactor corresponds to a preferred embodiment, in which it is possible to work with oxygenous cofeed. In a further preferred embodiment, the dehydrogenation is carried out in a tray reactor having 3 catalyst beds. In a method without oxygenous gas as cofeed, the reaction gas mixture is subjected to intermediate heating in the tray reactor on its way from one catalyst bed to the next catalyst bed, for example by passing it over heat exchanger plates heated by hot gases or by passing it through tubes heated by hot combustion gases.

In a preferred embodiment of the process according to the invention, the nonoxidative catalytic n-butane dehydrogenation is carried out autothermally. To this end, the reaction gas mixture of the n-butane dehydrogenation is additionally admixed with oxygen in at least one reaction zone and the hydrogen and/or hydrocarbon present in the reaction gas mixture is at least partially combusted, which generates directly in the reaction gas mixture at least a portion of the heat required for dehydrogenation in the at least one reaction zone.

In general, the amount of oxygenous gas added to the reaction gas mixture is selected in such a way that the amount of heat required for the dehydrogenation of n-butane is generated by the combustion of the hydrogen present in the reaction gas mixture and of any hydrocarbons present in the reaction gas mixture and/or of carbon present in the form of coke. In general, the total amount of oxygen supplied, based on the total amount of butane, is from 0.001 to 0.5 mol/mol preferably from 0.005 to 0.2 mol/mol, more preferably from 0.05 to 0.2 mol/mol. Oxygen may be used either in the form of pure oxygen or in the form of an oxygenous gas in a mixture with inert gases, for example in the form of air. The preferred oxygenous gas is air or oxygen-enriched air having an oxygen content of up to 50% by volume. The inert gases and the resulting combustion gases generally have an additional diluting action and thus promote the heterogeneously catalyzed dehydrogenation.

The hydrogen combusted to generate heat is the hydrogen formed in the catalytic n-butane dehydrogenation and also any hydrogen additionally added to the reaction gas mixture as hydrogenous gas. The amount of hydrogen present should preferably be such that the molar $H_2/O_2$ ratio in the reaction gas mixture immediately after the oxygen has been fed in is from 1 to 10 mol/mol, preferably from 2 to 5 mol/mol. In multistage reactors, this applies to every intermediate feed of oxygenous and any hydrogenous gas.

The hydrogen is combusted catalytically. The dehydrogenation catalyst used generally also catalyzes the combustion of the hydrocarbons and of hydrogen with oxygen, so that in principle no specialized oxidation catalyst is required apart from it. One embodiment works in the presence of one or more oxidation catalysts which selectively catalyze the combustion of hydrogen to oxygen in the presence of hydrocarbons. The combustion of these hydrocarbons with oxygen to give CO, $CO_2$ and water therefore proceeds only to a minor extent. The dehydrogenation catalyst and the oxidation catalyst are preferably present in different reaction zones.

When the reaction is carried out in more than one stage, the oxidation catalyst may be present only in one or in more than one reaction zone, or in all reaction zones.

Preference is given to disposing the catalyst which selectively catalyzes the oxidation of hydrogen at the points where there are higher partial oxygen pressures than at other points in the reactor, in particular near the feed point for the oxygenous gas. The oxygenous gas and/or hydrogenous gas may be fed in at one or more points in the reactor.

In one embodiment of the process according to the invention, there is intermediate feeding of oxygenous gas and of hydrogenous gas upstream of every tray of a tray reactor. In a further embodiment of the process according to the invention, oxygenous gas and, if appropriate, hydrogenous gas are fed in upstream of every tray except the first tray. In one embodiment, a layer of a specialized oxidation catalyst is present downstream of every feed point, followed by a layer of the dehydrogenation catalyst. In a further embodiment, no specialized oxidation catalyst is present. The dehydrogenation temperature is generally from 400 to 1100° C.; the pressure in the last catalyst bed of the tray reactor is generally from 0.2 to 5 bar, preferably from 1 to 3 bar. The GHSV is generally from 500 to 2000 $h^{-1}$, and in high-load operation, even up to 100 000 $h^{-1}$, preferably from 4000 to 16 000 $h^{-1}$.

A preferred catalyst which selectively catalyzes the combustion of hydrogen comprises oxides and/or phosphates selected from the group consisting of the oxides and/or phosphates of germanium, tin, lead, arsenic, antimony and bismuth. A further preferred catalyst which catalyzes the combustion of hydrogen comprises a noble metal of transition group VIII and/or I of the periodic table.

Typically, the heterogeneously catalyzed partial dehydrogenation of n-butane requires comparatively high reaction temperatures. The achievable conversion is limited by the thermodynamic equilibrium. Typical reaction temperatures are from 300 to 800° C. or from 400 to 700° C. High temperatures and removal of the $H_2$ reaction product shift the equilibrium position in the direction of the target product.

Since the heterogeneously catalyzed dehydrogenation reaction proceeds with increasing volume, the conversion may be increased by lowering the partial pressure of the products. This can be achieved in a simple manner, for example by dehydrogenating under reduced pressure and/or by admixing substantially inert diluent gases, for example steam which normally constitutes an inert gas for the dehydrogenation reaction. As a further advantage, dilution with steam generally causes reduced carbonization of the catalyst used, since the steam reacts with carbon formed by the principle of coal gasification. Further diluents suitable for the heterogeneously catalyzed butane dehydrogenation are, for example, CO, methane, ethane, $CO_2$, nitrogen and noble gases such as He, Ne and Ar. The diluents mentioned are generally also suitable as diluents in the $2^{nd}$ dehydrogenation zone.

It is favorable to carry out the nonoxidative n-butane dehydrogenation at a working pressure of from 0.1 to 3 bar and to dilute the n-butane-containing gas mixture to be dehydrogenated with steam. Thus, the steam firstly acts as a heat carrier and secondly reduces the product partial pressure, which has a favorable effect on the equilibrium position of the n-butane dehydrogenation. In addition, the use of steam has an advantageous effect on the lifetime of the noble metal-containing dehydrogenation catalysts. It is also possible to add hydrogen. The molar ratio of molecular hydrogen to n-butane is generally $\leq 5$. The molar ratio of steam to n-butane may be up to 30, appropriately from 0.1 to 2 and favorably from 0.5 to 1. One advantage of a procedure with low n-butane conversion is that, in single pass of the reaction gas mixture through the $1^{st}$ dehydrogenation zone, only a comparatively small amount of heat is consumed and comparatively low reaction temperatures are sufficient to achieve the conversion.

It is also possible to carry out the n-butane dehydrogenation (quasi-)adiabatically. In this case, the starting reaction gas mixture is generally heated initially to a temperature of from 450 to 700° C., (preferably from 550 to 650° C.), for example by direct firing of the reactor wall. In the case of adiabatic pass through the catalyst bed, the reaction gas mixture will then cool, depending on the conversion and dilution, by from about 30 to 200° C.

As the first dehydrogenation zone, a single shaft furnace reactor may be sufficient as the fixed bed reactor which is flowed through axially and/or radially by the reaction gas mixture.

In the simplest case, it is a single closed reaction volume, for example a vessel, whose internal diameter is from 0.1 to 10 m, possibly also from 0.5 to 5 m, and in which the fixed catalyst bed is applied to a support device (for example a grid). The reaction volume which is charged with catalyst and is substantially heat-insulated in adiabatic operation is flowed through axially by the hot n-butane-containing reaction gas. The catalyst geometry may either be spherical or else annular or strand-shaped. The n-butane-containing residual gas stemming from the $2^{nd}$ dehydrogenation zone may be injected via feed lines introduced into the catalyst bed. Since the reaction volume can be realized in this case by a very inexpensive apparatus, preference is to be given to all catalyst geometries which have a particularly low pressure drop. These are in particular catalysts which lead to a particularly large cavity volume or are structured, for example as monoliths or honeycombs. To realize a radial flow of the n-butane-containing reaction gas, the reactor may, for example, consist of two concentric cylindrical grids disposed in a shell and the catalyst bed may be arranged in their annular gap. In the adiabatic case, the shell would again be thermally insulated if appropriate.

After a prolonged operating time, the aforementioned catalysts can be regenerated in a simple manner, for example, by initially passing air (preferably) diluted with nitrogen and/or steam in first regeneration stages over the catalyst bed at an inlet temperature of from 300 to 600° C., frequently from 400 to 550° C. The catalyst hourly space velocity of regeneration gas (for example air) may be, for example, from 50 to 10 000 $h^{-1}$ and the oxygen content of the regeneration gas from 0.1 to 21% by volume. In subsequent further regeneration stages, the regeneration gas used under otherwise identical regeneration conditions may be air. Suitable regeneration gases are also flue gases which have a residual oxygen content of from 1 to 6% by volume and are formed in the combustion, and still comprise nitrogen, steam, carbon oxides and residual hydrocarbon. It is recommended to flush the catalyst before it is regenerated with inert gas (for example $N_2$). It is generally to be recommended to subsequently regenerate with pure hydrogen or with hydrogen diluted by inert gas (preferably steam) (the hydrogen content should be $\leq 1\%$ by volume).

The heterogeneously catalyzed, nonoxidative n-butane dehydrogenation may be operated with comparatively low butane conversion ($\leq 15$ mol %); in this case, the high selectivity and catalyst lifetime are advantageous. The n-butane dehydrogenation should preferably be operated at conversions of >15 mol %, more preferably >30 mol %. The hourly space velocity of reaction gas may, for example, be from 100 to 10 000 or 40 000 $h^{-1}$, for example from 300 to 7000 $h^{-1}$ or from about 500 to 4000 $h^{-1}$.

In the simplest case, the fixed catalyst beds in a shaft furnace reactor are arranged axially or in the annular gaps of concentric cylindrical grids. However, it is also possible to arrange the annular gaps in segments one on top of another and to conduct the gas after it has passed radially through one segment into the next segment above it or below it.

Appropriately, the reaction gas mixture is subjected to intermediate heating in the tray reactor on its path from one catalyst bed to the next catalyst bed, for example by passing it over heat exchanger surfaces (e.g. ribs) heated by hot gases or by passing it through pipes heated by hot combustion gases.

When the tray reactor is otherwise operated adiabatically, it is sufficient for butane conversions of $\leq 30$ mol %, in particular when using the catalysts described in DE-A 199 37 107, especially those of the exemplary embodiments, to conduct the reaction gas mixture into the dehydrogenation reactor preheated to a temperature of from 450 to 550° C. and to keep it within this temperature range inside the tray reactor. For higher butane conversions, the reaction gas mixture is appropriately conducted into the dehydrogenation reactor preheated to higher temperatures (these may be up to 700° C.) and kept within this elevated temperature range inside the tray reactor.

It is even more elegant to carry out the above-outlined intermediate heating in a direct way (autothermal method). To this end, a limited amount of molecular oxygen is added to the reaction gas mixture either before it flows through the first catalyst bed (in that case the starting reaction gas mixture should comprise added molecular hydrogen) and/or between the downstream catalyst beds. It is thus possible (generally catalyzed by the dehydrogenation catalysts themselves) to bring about a limited combustion of molecular hydrogen which is present in the reaction gas mixture, has been formed in the course of the heterogeneously catalyzed n-butane dehydrogenation and/or has been added to the reaction gas mixture. It may be appropriate to provide catalyst beds in the tray reactor which are charged with a catalyst which selectively catalyzes the combustion of hydrogen. Examples of useful catalysts include those of the documents U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314; for example, these and the dehydrogenation catalyst may be arranged in the tray reactor in alternating catalyst beds.

In general, the oxygen feeding as described above is undertaken in such a way that the oxygen content of the reaction gas mixture, based on the amount of molecular hydrogen contained therein, is from 0.5 to 50% by volume, preferably from 10 to 25% by volume. Useful oxygen sources include both pure molecular oxygen and oxygen diluted with inert gas, for example CO, $CO_2$, $N_2$ and/or noble gases, but especially also air and oxygen-enriched air. The resulting combustion gases generally have an additional diluting effect and thus promote heterogeneously catalyzed n-butane dehydrogenation.

The isothermicity of the heterogeneously catalyzed n-butane dehydrogenation can be further improved by incorporating closed internals in the spaces between the catalyst beds in the tray reactor. These internals comprise suitable solids or liquids which evaporate or melt above a certain temperature, consuming heat as they do so, and, when the temperature falls below this value, condense again and thereby release heat.

Another means of heating the gas mixture fed to the first dehydrogenation zone to the reaction temperature required for the heterogeneously catalyzed butane dehydrogenation in the first dehydrogenation zone is to add molecular hydrogen to it and combust it by means of molecular oxygen over suitable specific combustion catalysts, and bringing about the heating to the desired reaction temperature by means of the heat of combustion thus released. The resulting combustion products such as $CO_2$, $H_2O$, and the $N_2$ which is in some cases present in the molecular oxygen required for the combustion, are advantageous inert diluent gases.

In one embodiment of the invention, oxygeneous gas is fed, if appropriate, inteiinediately upstream of each tray of the tray reactor. In a further embodiment of the process according to the invention, oxygeneous gas is fed upstream of each tray except for the first tray. In a further embodiment of the process according to the invention, a bed of specific oxidation catalyst suitable for the $H_2$ oxidation is present downstream of each oxygen feed point, followed by a bed of dehydrogenation catalyst. If required, external molecular hydrogen (in pure form or diluted with inert gas) may, if appropriate, additionally be fed upstream of each tray. In a less preferred embodiment, the catalyst beds may also comprise mixtures of dehydrogenation and $H_2$ oxidation catalysts.

The dehydrogenation temperature in the tray reactor is generally from 400 to 800° C., the pressure generally from 0.2 to 10 bar, preferably from 0.5 to 4 bar and more preferably from 1 to 3 bar. The overall gas hourly space velocity (GHSV) is generally from 500 to 10 000 $h^{-1}$, in high-load operation even up to 80 000 $h^{-1}$, regularly from 30 000 $h^{-1}$ to 40 000 $h^{-1}$.

In principle, useful dehydrogenation catalysts for the heterogeneously catalyzed n-butane dehydrogenation are all dehydrogenation catalysts known in the prior art. They can be divided roughly into two groups: into those which are of oxidic nature (for example chromium oxide and/or aluminum oxide) and into those which comprise at least one noble metal deposited on a generally oxidic support. Among others, it is thus possible to use all dehydrogenation catalysts which are described in WO 01/96270, EP-A 731077, DE-A 10211275, DE-A 10131297, WO 99/46039, U.S. Pat. No. 4,788,371, EP-A-0 705 136, WO 99/29420, U.S. Pat. No. 4,220,091, U.S. Pat. No. 5,430,220, U.S. Pat. No. 5,877,369, EP-A-0 117 146, DE-A 199 37 196, DE-A 199 37 105 and DE-A 199 37 107.

The dehydrogenation catalysts used generally comprise a support and an active composition. The support generally consists of a beat-resistant oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof, as a support. The mixtures may be physical mixtures or else chemical mixed phases such as magnesium aluminum oxide or zinc aluminum oxide mixed oxides. Preferred supports are zirconium dioxide and/or silicon dioxide, and particular preference is given to mixtures of zirconium dioxide and silicon dioxide.

These are, for example, dehydrogenation catalysts which comprise from 0 to 99.9% by weight of zirconium dioxide, from 0 to 60% by weight of aluminum oxide, silicon dioxide and/or titanium dioxide and from 0.1 to 10% by weight of at least one element of the first or second main group (more preferably potassium and/or cesium), of an element of the third transition group, of an element of the eighth transition group of the Periodic Table of the Elements (more preferably platinum and/or palladium), lanthanum and/or tin, with the proviso that the sum of the percentages by weight is 100% by weight.

For example, the dehydrogenation catalysts are present in the form of catalyst extrudates (diameter typically from 1 to 10 mm, preferably from 1.5 to 5 mm; length typically from 1 to 20 mm, preferably from 3 to 10 mm), tablets (preferably with similar dimensions to the extrudates) and/or catalyst rings (external diameter and length in each case typically from 2 to 30 mm, for example from 2 to 10 mm, wall thickness appropriately from 1 to 10 mm, for example from 1 to 5 mm or from 1 to 3 mm).

In general, the dehydrogenation catalysts (for example those described in DE-A 19937107) catalyze both the dehydrogenation of nubutane and the combustion of molecular hydrogen.

The active compositions of the dehydrogenation catalysts generally comprise one or more elements of transition group VIII of the periodic table, preferably platinum and/or palladium, more preferably platinum. Furthermore, the dehydrogenation catalysts may comprise one or more elements of main group I and/or II, preferably potassium and/or cesium. The dehydrogenation catalysts may further comprise one or more elements of transition group III including the lanthanides and actinides, preferably lanthanum and/or cerium. Finally, the dehydrogenation catalysts may comprise one or more elements of main group III and/or IV, preferably one or more elements selected from the group consisting of boron, gallium, silicon, germanium, tin and lead, more preferably tin.

In a preferred embodiment, the dehydrogenation catalyst comprises at least one element of transition group VIII, at least one element of main group I and/or II, at least one element of main group III and/or IV and at least one element of transition group m including the lanthanides and actinides.

For example, all dehydrogenation catalysts which are disclosed in WO 99/46039, U.S. Pat. No. 4,788,371, EP-A 705 136, WO 99/29420, U.S. Pat. No. 5,220,091, U.S. Pat. No. 5,430,220, U.S. Pat. No. 5,877,369, EP 0 117 146, DE-A 199 37 106, DE-A 199 37 105 and DE-A 199 37 107 may be used in accordance with the invention. Particularly preferred catalysts for the above-described variants of the autothermal n-butane dehydrogenation are the catalysts according to examples 1, 2, 3 and 4 of DE-A 199 37 107.

It is characteristic of the heterogeneously catalyzed, non-oxidative dehydrogenation of n-butane that it proceeds endothermically. This means that the heat energy required for the attainment of the required reaction temperature for the reaction has to be supplied to the starting gas mixture either before and/or in the course of the heterogeneously catalyzed dehydrogenation. If appropriate, the reaction gas mixture will withdraw the heat of reaction required from itself.

In addition, it is typical of heterogeneously catalyzed, non-oxidative dehydrogenation of n-butane, owing to the high reaction temperatures required, that small amounts of high-boiling, high molecular weight organic compounds and carbon are formed and are deposited on the catalyst surface, thus deactivating it. In order to counteract this deactivation, the n-butane-containing reaction gas mixture can be diluted with steam. Carbon which is deposited is partly or fully converted under these conditions by the principle of coal gasification.

Another means of eliminating deposited carbon compounds from the catalyst surface consists in charging the dehydrogenation catalyst with an oxygen-containing gas (appropriately in the absence of hydrocarbons) from time to time at elevated temperature and thus burning off the deposited carbon. However, substantial suppression of the formation of carbon deposits on the catalyst is also possible by adding molecular hydrogen to the n-butane to be dehydrogenated before it is contacted with the dehydrogenation catalyst.

It is also possible to add a mixture of steam and molecular hydrogen to the n-butane to be dehydrogenated. Addition of molecular hydrogen also minimizes the formation of allenes (1,2-butadiene, propadiene), butynes, propyne and acetylene as by-products.

Preference is given to carrying out the nonoxidative n-butane dehydrogenation in the presence of steam. The added steam serves as a heat carrier and supports the gasification of organic deposits on the catalysts, which counteracts carbonization of the catalysts and increases the lifetime of the catalysts. The organic deposits are converted to carbon monoxide, carbon dioxide and in some cases water.

The dehydrogenation catalyst may be regenerated in a manner known per se. For instance, steam may be added to the reaction gas mixture or a gas comprising oxygen may be passed from time to time over the catalyst bed at elevated temperature and the deposited carbon burnt off. The dilution with steam shifts the equilibrium toward the products of dehydrogenation. After the regeneration, the catalyst is, if appropriate, reduced with a hydrogenous gas.

The nonoxidative catalytic n-butane dehydrogenation affords a gas mixture which, in addition to butadiene, 1-butene, 2-butene and unconverted n-butane, comprises secondary constituents. Customary secondary constituents are hydrogen, steam, nitrogen, CO and $CO_2$, methane, ethane, ethene, propane and propene. The composition of the gas mixture leaving the first dehydrogenation zone can vary greatly depending on the method of dehydrogenation. For instance, when the preferred autothermal dehydrogenation with feeding of oxygen is carried out, the product gas mixture comprises a comparatively high content of steam and carbon oxides. In methods without feeding of oxygen, the product gas mixture of the nonoxidative dehydrogenation has a comparatively high content of hydrogen.

The product gas stream b of the nonoxidative autothermal n-butane dehydrogenation typically comprises from 0.1 to 15% by volume of butadiene, from 1 to 20% by volume of 1-butene, from 1 to 35% by volume of 2-butene (cis/trans-2-butene), from 20 to 80% by volume of n-butane, from 1 to 70% by volume of steam, from 0 to 10% by volume of low-boiling hydrocarbons (methane, ethane, ethene, propane and propene), from 0.1 to 40% by volume of hydrogen, from 0 to 70% by volume of nitrogen and from 0 to 15% by volume of carbon oxides.

The product gas stream b leaving the first dehydrogenation zone is preferably separated into two substreams, in which case only one of the two substreams is subjected to the further process parts C to F and the second substream can be recycled into the first dehydrogenation zone. An appropriate procedure is described in DE-A 102 11 275. However, it is also possible to subject the entire product gas stream b of the nonoxidative catalytic n-butane dehydrogenation to the further process parts C to F.

According to the invention, the nonoxidative catalytic dehydrogenation is followed downstream by an oxidative dehydrogenation (oxydehydrogenation) as process part C. This essentially dehydrogenates 1-butene and 2-butene to 1,3-butadiene, and 1-butene is generally virtually fully depleted.

This may in principle be carried out in all reactor types and methods known from the prior art, for example in a fluidized bed, in a tray furnace, in a fixed bed tubular or tube bundle reactor, or in a plate heat exchanger reactor. Preference is given to using the latter in the process according to the invention. To carry out the oxidative dehydrogenation, a gas mixture is required which has a molar oxygen:n-butenes ratio of at least 0.5. Preference is given to working at an oxygen n-butenes ratio of from 0.55 to 50. To attain this value, the product gas mixture stemming from the nonoxidative catalytic dehydrogenation is generally mixed with oxygen or an oxygenous gas, for example air. The resulting oxygenous gas mixture is then sent to the oxydehydrogenation.

Suitable processes are described, for example, in WO-A 2004007408, DE 10361822, DE 10361823 and DE 10361824.

The documents WO 01/96270, DE-A 10245585, DE-A 10246119, DE-A 10313210, DE-A 10313214, DE-A 10313213, DE-A 10313212, DE-A 10308824, DE-A 10313208 and DE-A 10211275 describe processes for preparing acrolein or acrylic acid from propane or propene and suitable reactors and catalysts, as may also be used analogously for the preparation of butadiene. DE-A 10137534 describes reactors and catalysts suitable for the partial steps of the preparation of maleic anhydride starting from a mixture comprising n-butenes, which may also be used correspondingly in the process according to the invention. In this case, the oxidizing agent used may be pure molecular oxygen, air, oxygen-enriched air or any other mixture of oxygen and inert gas.

The charge gas mixture which is fed into the second dehydrogenation zone preferably has the following composition; cf. also WO-A 04/07408, DE-A 102 45 585 and DE-A 102 46 119. Thus, the molar n-butane-n-butenes:$N_2$:$O_2$:$H_2O$:others ratios=0.5 to 20:1:0.1 to 40:0.1 to 10:0 to 20:0 to 1, for example=1 or 2 to 10:1:0.5 to 20:0.5 to 5:0.01 to 10:0 to 1 or else=3 to 6:1:1 to 10:1 to 3:0.1 to 2:0 to 0.5. The hourly space velocity (1 (STP)/l·h) on the oxidation catalyst of reaction gas is frequently from 1500 to 2500 $h^{-1}$ or to 4000 $h^{-1}$. The hourly space velocity of butenes may be from 50 or 80 to 200 or 300 and more 1 (STP)/l·h.

The catalysts which are particularly suitable for the oxydehydrogenation are generally based on an Mo—Bi—O-containing multimetal oxide system which generally additionally comprises iron. In general, the catalyst system also comprises further additional components from groups 1 to 15 of the Periodic Table, for example potassium, magnesium, zirconium, chromium, nickel, cobalt, cadmium, tin, lead, germanium, lanthanum, manganese, tungsten, phosphorus, cerium, aluminum or silicon.

Suitable catalysts for the oxydehydrogenation are disclosed by DE-A 44 31 957, the German patent application DE 102004025445 which was yet to be published at the priority date of the present application and DE-A 44 31 949. This is especially true of those of the general formula I in both of the aforementioned documents. Particularly advantageous catalysts for the oxydehydrogenation are disclosed by the documents DE-A 103 25 488, DE-A 103 25 487, DE-A 103 53 94, DE-A 103 44 149, DE-A 103 51 269, DE-A 103 50 812, DE-A 103 50 822.

Suitable catalysts and their preparation are described, for example, in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409

($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x$+$SiO_2$) and DE-A 24 40 329 ($Mo_{12}BiCo_{4.5}Ni_{2.5}Cr_3P_{0.5}K_{0.1}O_x$).

Suitable catalysts are in particular the multimetal oxide active compositions of the general formula I of DE-A 199 55 176, the multimetal oxide active compositions of the general formula I of DE-A 199 48 523, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168 and also the multimetal oxide active compositions specified in EP-A 0 700 714.

Also suitable for this oxidation step are the multimetal oxide catalysts comprising Mo, Bi and Fe which are disclosed in the documents DE-A 100 46 957, DE-A 100 63 162, DE-C 33 38 380, DE-A 199 02 562, EP-A 15 565, DE-C 23 80 765, EP-A 807 465, EP-A 27 9374, DE-A 33 00 044, EP-A 575 897, U.S. Pat. No. 4,438,217, DE-A 198 55 913, WO 98/24746, DE-A 197 46 210 (those of the general formula II), JP-A 91/294239, EP-A 293 224 and EP-A 700 714. This applies in particular to the exemplary embodiments in these documents, and among these particular preference is given to those of WO-A 04/07408, EP-A 15 565, EP-A 575 897, DE-A 197 46 210 and DE-A 198 55 913. Particular emphasis is given in this context to the catalyst according to example 1c from EP-A 15 565 and also to a catalyst to be prepared in a corresponding manner but whose active composition has the composition $Mo_{12}Ni_{6.5}Zn_2Fe_2Bi_1P_{0.006}K_{0.06}O_x \cdot 10SiO_2$. Emphasis is also given to the according to example 3 from DE-A 198 55 913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to example 1 of DE-A 197 46 210. Also suitable are the multimetdi oxide catalysts of U.S. Pat. No. 4,438,217. The latter hollow cylinders preferably have the following dimensions: 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further suitable catalyst geometries are extrudates (for example length 7.7 mm and diameter 7 mm; or length 6.4 mm and diameter 5.7 mm).

A multitude of the multimetal oxide active compositions suitable for the oxydehydrogenation of n-butenes to butadiene can be encompassed by the general formula IV $$Mo_{12}Bi_aFe_bX^1_cX^2_dX^3_eX^4_fO_n \qquad (IV)$$

in which the variables are each defined as follows:
$X^1$=nickel and/or cobalt,
$X^2$=thalium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

They are obtainable in a manner known per se (see, for example, DE-A 40 23 239) and are customarily shaped in substance to give spheres, rings or cylinders or else used in the form of coated catalysts, i.e. preshaped inert support bodies coated with the active composition. It will be appreciated that they may also be used as catalysts in powder form.

In principle, active compositions of the general formula IV can be prepared in a simple manner by, starting from suitable sources of their elements, obtaining a very intimate, preferably finely divided dry mixture having a composition corresponding to the elemental stoichiometry and calcining it at temperatures of from 350 to 650° C. The calcination may be effected either under inert gas or under an oxidizing atmosphere, for example air (or a mixture of inert gas and oxygen) or under a reducing atmosphere (for example a mixture of inert gas, $NH_3$, CO and/or $H_2$). The calcination time can be from a few minutes to a few hours and typically decreases with increasing temperature. Useful sources for the elemental constituents of the multimetal oxide active compositions IV are oxides or compounds which can be converted to oxides by heating, at least in the presence of oxygen.

In addition to the oxides, useful starting compounds include in particular halides, nitrates, formates, oxalates, citrates, acetates, carbonates, anine complexes, ammonium salts and/or hydroxides. Compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture.

The starting compounds for preparing multimetal oxide active compositions IV can be intimately mixed in the dry or in the wet state. When they are mixed in the dry state, the starting compounds are appropriately used in the form of finely divided powders and subjected to calcination after mixing and, if appropriate, compacting. However, preference is given to intimate mixing in the wet state. Customarily, the starting compounds are mixed with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the resulting aqueous composition is dried, and the drying process is preferably effected by spray-drying the aqueous mixture at exit temperatures of from 100 to 150° C.

The multimetal oxide active compositions of the general formula IV may be used in the oxidative dehydrogenation either in powder form or shaped to certain catalyst geometries, and the shaping may be effected either before or after the final calcination. For example, unsupported catalysts can be prepared from the powder form of the active composition or its uncalcined or partially calcined precursor composition by compacting and shaping (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries include solid cylinders or hollow cylinders having an external diameter and a length of from 2 to 10 mm. In the case of the hollow cylinder, a wall thickness of from 1 to 3 mm is appropriate. The unsupported catalyst can also have spherical geometry, in which case the spherical diameter can be from 2 to 10 mm.

A particularly favorable hollow cylinder geometry has the dimensions 5 mm×3 mm×2 mm (external diameter×length×internal diameter), especially in the case of unsupported catalysts.

The pulverulent active composition or its pulverulent precursor composition which is yet to be calcined and/or has only been partly calcined may also be shaped by applying to preshaped inert catalyst supports. The coating of the support bodies to produce coated catalysts is generally performed in a suitable rotatable vessel, as disclosed, for example, by DE-A 29 09 671, EP-A 293 859 or EP-A 714 700. To coat the support bodies, the powder composition to be applied is appropriately moistened and dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are the customary porous or non-porous aluminum oxides, silicon dioxide, thorium dioxide, zirconium dioxide, silicon carbide or silicates such as magnesium silicate or aluminum silicate. They behave substantially inertly. The support bodies can have a regular or irregular shape, although preference is given to regularly shaped support bodies having distinct surface roughness, for example spheres or hollow cylinders. It is suitable to use substantially nonporous, surface-roughened spherical steatite supports whose diameter is from 1 to 10 mm or from 1 to 8 mm, preferably from 4 to 5 mm. However, it is also suitable to use cylinders as support bodies, whose length is from 2 to 10 mm and whose external diameter is from 4 to 10 mm. In the case of rings suitable in accordance with the invention as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Support bodies suitable in accordance with the invention are in particular also rings of geometry 7 mm×3 mm×4 mm (external diameter×length×internal diameter). The fineness of the catalytically active oxide compositions to be applied to the surface of the support body is adapted to the desired coating thickness; cf. also EP-A 714 700.

Multimetal oxide active compositions to be used for the oxydehydrogenation of n-butenes to butadiene are also compositions of the general formula V

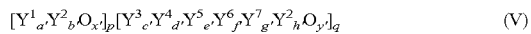
(V)

in which the variables are each defined as follows:
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from 0.001 to 20,
f'=from 0 to 6,
g'=from 0 to 15,
h'=from 8 to 16,
x',y'=numbers which are determined by the valency and frequency of the elements in V other than oxygen and
p,q=numbers whose p/q ratio is from 0.1 to 10, comprising three-dimensional regions of the chemical composition $Y^1.Y^2_{b'}O_{x'}$ which are delimited from their local environment owing to their different composition, and whose maximum diameter (longest direct line passing through the center of the region and connecting two points on the surface (interface) of the region) is from 1 nm to 100 μm, frequently from 10 nm to 500 nm or from 1 μm to 50 or 25 μm.

Particularly advantageous inventive multimetal oxide compositions V are those in which $Y^1$ is only bismuth.

Among these, preference is given in turn to those of the general formula VI

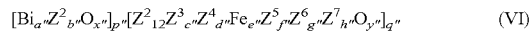
(VI)

in which the variables are each defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably from 0.1 to 3,
f"=from 0 to 5,
g"=from 0 to 10,
h"=from 0 to 1,
x",y"=numbers which are determined by the vatency and frequency of the elements in VI other than oxygen,
p",q"=numbers whose p"/q" ratio is from 0.1 to 5, preferably from 0.5 to 2,
and very particular preference is given to those compositions VI in which $Z^2_{b''}$=(tungsten)$_{b''}$ and $Z^2_{12}$=(molybdenum)$_{12}$.

It is also advantageous when at least 25 mol % (preferably at least 50 mol % and more preferably at least 100 mol %) of the total proportion of $[Y^1_{a'}Y^2_{b'}O_{x'}]_p$ ($[Bi_{a''}Z^2_{b''}O_{x''}]_{p''}$) of the multimetal oxide compositions V or of the multimetal oxide compositions VI is in the form of three-dimensional regions of the chemical composition $Y^1_{a'}Y^2_{b'}O_{x'}$ [$Bi_{a''}Z^2_{b''}O_{x''}$] which are delimited from their local environment owing to their different chemical composition, and whose maximum diameter is in the range from 1 nm to 100 μm.

The preparation of multimetal oxide active compositions V is described, for example, in EP-A 575 897 and also in DE-A 19 855 913.

The inert support materials recommended above are also useful, inter alia, as inert materials for the dilution and/or delimitation of the appropriate fixed catalyst beds from one another, or as a preliminary bed which protects them and/or heats the gas mixture.

The oxydehydrogenation is generally carried out at a temperature of from 220 to 490° C. and preferably from 250 to 450° C. A reactor inlet pressure is selected which is sufficient to overcome the flow resistances in the plant and the subsequent workup. This reactor inlet pressure is generally from 0.005 to 1 MPa gauge, preferably from 0.01 to 0.5 MPa gauge. By its nature, the gas pressure applied in the inlet region of the reactor falls off substantially over the entire catalyst bed.

The oxydehydrogenation of n-butenes to butadiene may be carried out with the catalysts described, for example, in a one-zone multiple catalyst tube fixed bed reactor as described in DE-A 44 31 957.

The oxidizing agent used is generally oxygen. When $N_2$ is selected as the inert diluent gas, it is found to be particularly advantageous to use air or oxygen-enriched air as the oxygen source.

Frequently, an n-butenes:oxygen:inert gases (including steam) volume (l (STP)) ratio of 1:(1.0 to 3.0):(5 to 25), preferably 1:(1.7 to 2.3):(10 to 15) is employed. The reaction pressure is typically in the range from 1 to 3 bar and the total hourly space velocity is preferably from 1500 to 4000 or 6000 l (STP)/l·h or more. The loading based on n-butenes is typically from 90 to 200 l (STP)/l·h or to 300 l (STP)/l·h or more.

The flow of the charge gas mixture to the one-zone multiple catalyst tube fixed bed reactor is preferably from above. The heat exchange medium used is appropriately a salt melt, preferably consisting of 60% by weight of potassium nitrate ($KNO_3$) and 40% by weight of sodium nitrite ($NaNO_2$) or of 53% by weight of potassium nitrate ($KNO_3$), 40% by weight of sodium nitrite ($NaNO_2$) and 7% by weight of sodium nitrate ($NaNO_3$).

Viewed over the reactor, salt mekl and reaction gas mixture may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes from bottom to top with catalyst as follows (for flow from bottom to top, the charge sequence should appropriately be reversed):

first, to a length of from 40 to 80 or to 60% of the catalyst tube length, either only catalyst or a mixture of catalyst and inert material, the latter, based on the mixture, making up a proportion by weight of up to 20% by weight (section C);

following this, to a length of from 20 to 50 or to 40% of the total tube Length, either only catalyst or a mixture of catalyst and inert material, the latter, based on the mixture, making up a proportion by weight of up to 40% by weight (section B); and finally, to a length of from 10 to 20% of the total tube length, a bed of inert material (section A) which is preferably selected such that it causes a minimum pressure drop.

Section C is preferably undiluted.

The aforementioned charge variant is especially appropriate when the catalysts used are those according to example 3 of WO-A 04/07408, example 1 of DE-A 100 46 957 or according to example 3 of DE-A 100 46 957 and the inert material used is steatite rings having the geometry 7 mm×7 mm×4 mm (external diameter×height×internal diameter). With regard to the salt bath temperature, the statements made in DE-A 44 31 957 apply.

However, the oxydehydrogenation of n-butenes to butadiene may also be carried out with the catalysts described in a two-zone multiple catalyst tube fixed bed reactor as described in DE-A 199 10 506. In both of the above-described cases, the conversion of n-butenes achieved in single pass is normally ≧85 mol %, or ≧90 mol % or ≧95 mol %.

The salt bath temperature of multiple catalyst tube reactors for the oxydehydrogenation of n-butenes to butadiene is generally from 300 to 400° C. In addition, the heat exchange media (preferably salt melts) are normally conducted through the multiple catalyst tube fixed bed reactors in such amounts that the difference between their inlet and their outlet temperature is generally ≦5° C.

It should also be mentioned that the oxydehydrogenation may be carried out in such a way that a reaction gas mixture which does not comprise any oxygen is initially passed over the catalyst bed. In this case, the oxygen required for the oxydehydrogenation is provided in the form of lattice oxygen. In a subsequent regeneration step with an oxygen-containing gas (for example air, oxygen-etiriched air or oxygen-depleted air), the catalyst bed is regenerated in order in turn to provide an oxygen-free reaction gas mixture.

Instead of tube bundle reactors, it is also possible to use plate heat exchanger reactors with salt cooling and/or evaporative cooling, as described, for example, in DE-A 19 929 487 and DE-A 19 952 964, or fluidized bed reactors.

In principle, the first and the second dehydrogenation zone in the process according to the invention may also be configured as described in WO-A 04007408, DE-A 19 837 517, DE-A 19 9105 06, DE-A 19 910 508 and DE-A 19 837 519. Typically, the external heating in the two dehydrogenation zones, if appropriate in multizone reactor systems, is adjusted in a manner known per se to the specific reaction gas mixture composition and catalyst charge.

In this case, an excess of molecular oxygen generally has an advantageous effect on the kinetics of the dehydrogenation. Since, in contrast to the conditions in the first dehydrogenation zone (nonoxidative dehydrogenation), the oxydehydrogenation of n-butenes to butadiene is subject to kinetic control, it is also possible in the second dehydrogenation zone (oxydehydrogenation) to work with a molar excess of n-butenes over molecular oxygen. In this case, the excess n-butenes also assume the role of a diluent gas.

The source used for the molecular oxygen required in the oxydehydrogenation, which is, for example, admixed to product gas mixture b before it is charged to the second dehydrogenation may either be pure molecular oxygen or molecular oxygen diluted with inert gas such as $CO_2$, CO, noble gases, $N_2$ and/or saturated hydrocarbons. Appropriately, the oxygen source used at least to cover part of the requirement for molecular oxygen will be air.

Metering of cold air to hot product gas mixture b allows it to be cooled to the temperature required for the oxydehydrogenation.

In the long-term operation of the two dehydrogenation zones, a lowering of the catalyst quality (especially with regard to activity and selectivity) of the catalysts present in the reaction zones will normally occur. One way of counteracting this is to regenerate the particular catalyst bed from time to time (to this end, it is also possible in the oxidation zone, for example, to conduct residual gas at elevated temperature over the catalyst bed of the oxidation catalyst), as described, for example, in the documents DE-A 10351269, DE-A 10350812 and DE-A 10350822. It is also possible to increase the reaction temperature over the operating time in order to compensate for a reduced catalyst activity. However, it has surprisingly been found to be advantageous in both dehydrogenation zones to increase the particular working pressure in the gas phase, based on an identical hourly space velocity on the particular catalyst bed of reaction gas mixture in l (STP)/l·h, during the operating time of the catalyst bed, in order to further counteract the deactivation of the catalyst beds, as described, for example, in the German patent application DE 102004025445 which was yet to be published at the priority date of the present application. For this purpose, it is possible to mount at a suitable point a pressure regulating device (in the simplest case a throttle device, for example a throttle valve or else a vane regulator), for example also partially permeable perforated diaphragms whose holes may successively be partly or fully closed. It is in principle sufficient to introduce the pressure regulating device at a suitable point in the flow path of the reaction gas mixture whence the pressure increase can propagate into the reaction zones as a result of backpressure. Typical pressure increases undertaken (which may be undertaken continuously according to the deactivation, but also discontinuously) in the course of the operating time may be up to 3000 mbar and more.

The coupling of the nonoxidative catalytic, preferably autothermal, dehydrogenation with the oxidative dehydrogenation of the n-butenes formed results in a very much higher yield of butadiene, based on n-butane used, being obtained. In addition, the nonoxidative dehydrogenation may be operated more gently. Comparable butadiene yields would be achievable with an exclusively nonoxidative dehydrogenation only at the cost of distinctly lower selectivities. In the case of exclusively oxidative dehydrogenation, only low n-butane conversions are achieved.

In addition to butadiene and unconverted n-butane, the product gas stream c leaving the oxidative dehydrogenation also comprises 2-butene and steam. As secondary constituents, it generally comprises carbon monoxide, carbon dioxide, oxygen, nitrogen, methane, ethane, ethene, propane and propene, with or without hydrogen and oxygenous hydrocarbons, known as oxygenates. In general, it comprises only small proportions of 1-butene.

Oxygenous hydrocarbons (oxygenates) are, for example, lower aldehydes, lower alkanecarboxylic acids (e.g. acetic acid, formic acid and propionic acid) and maleic anhydride, benzaldehyde, aromatic carboxylic acids and aromatic carboxylic anhydrides (e.g. phthalic anhydride and benzoic acid).

In general, the product gas stream c leaving the oxidative dehydrogenation comprises from 1 to 50% by volume of butadiene, from 20 to 80% by volume of n-butane, from 0.5 to 40% by volume of 2-butene, from 0 to 20% by volume of 1-butene, from 0 to 70% by volume of steam, from 0 to 10% by volume of low-boiling hydrocarbons (methane, ethane, ethene, propane and propene), from 0.1 to 40% by volume of hydrogen, from 0 to 70% by volume of nitrogen, from 0 to 10% by volume of carbon oxides and from 0 to 10% by volume of oxygenates. Oxygenates may, for example, be furan, acetic acid, maleic anhydride, formic acid or butyraldehyde.

In one process part, D, the low-boiling secondary constituents other than the $C_4$ hydrocarbons (n-butane, isobutane, 1-butene, cis-/trans-2-butene, isobutene, butadiene) are removed at least partly, but preferably substantially fully, from the product gas stream of the n-butane dehydrogenation to obtain a $C_4$ product gas stream d.

In one embodiment of the process according to the invention, in process part D, water is initially removed from product gas stream c. Water may be removed, for example, by condensing out, by cooling and/or compressing product gas stream c, and may be carried out in one or more cooling and/or compression stages.

The low-boiling secondary constituents may be removed from the product gas stream by customary separation processes such as distillation, rectification, membrane processes, absorption or adsorption.

To remove the hydrogen present in product gas stream c, the product gas mixture, after it has been cooled if appropriate, for example in an indirect heat exchanger, may be passed through a membrane, generally configured as a tube, which is permeable only to molecular hydrogen. The thus removed molecular hydrogen may, if required, be used at least partly in the dehydrogenation or sent to another utilization, for example to the generation of electrical energy in fuel cells.

The carbon dioxide present in product gas stream c may be removed by $CO_2$ gas scrubbing. The carbon dioxide gas scrubbing may precede a special combustion stage in which carbon monoxide is oxidized selectively to carbon dioxide.

In a preferred embodiment of the process according to the invention, the gas stream c is compressed in at least one first compression stage and subsequently cooled to condense out at least one condensate stream comprising water and leave a gas stream c' comprising n-butane, n-butenes, butadiene, hydrogen and steam, with or without carbon oxides and with or without inert gases.

The compression may be effected in one or more stages. Overall, compression is effected from a pressure in the range from 1.0 to 4.0 bar to a pressure in the range from 3.5 to 20 bar. Each compression stage is followed by a cooling stage in which the gas stream is cooled to a temperature in the range from 15 to 60° C. The aqueous condensate stream may thus comprise several streams in the case of multistage compression.

The gas stream c' generally consists substantially of $C_4$ hydrocarbons (essentially n-butane, 2-butene and butadiene), hydrogen, carbon dioxide and steam. In addition, stream c' may also comprise low boilers, inert gases (nitrogen) and carbon oxides as further secondary components. The aqueous condensate stream consists generally to an extent of at least 50% by weight, preferably to an extent of at least 90% by weight, of water, and additionally comprises, to a small extent, low boilers, $C_4$ hydrocarbons, oxygenates and carbon dioxide.

Suitable compressors are, for example, turbocompressors and piston compressors including rotary piston compressors. The compressors may be driven, for example, by an electric motor, an expander or a gas or steam turbine. Typical compression ratios (outlet pressure:inlet pressure) per compression stage are, depending on the design, between 1.5 and 3.0.

The compressed gas is cooled with heat exchangers which may be designed, for example, as tube bundle, spiral or plate heat exchangers. The coolants used in the heat exchangers are cooling water or heat carrier oils. In addition, preference is given to using air cooling with the use of fans.

In a preferred embodiment of the process according to the invention, the uncondensable or low-boiling gas constituents such as hydrogen, oxygen, carbon oxides, the low-boiling hydrocarbons (methane, ethane, ethene, propane, propene) and any nitrogen are removed by means of a high-boiling absorbent in an absorption/desorption cycle to obtain a $C_4$ product gas stream d which consists substantially of the $C_4$ hydrocarbons. In general, the $C_4$ product gas stream d consists to an extent of at least 80% by volume, preferably to an extent of at least 90% by volume, more preferably to an extent of at least 95% by volume, of the $C_4$ hydrocarbons. Stream d consists substantially of n-butane, 2-butene and butadiene.

To this end, in an absorption stage, product gas stream c, after preceding water removal, is contacted with an inert absorbent and the $C_4$ hydrocarbons are absorbed in the inert absorbent to obtain absorbent laden with $C_4$ hydrocarbons and an offgas comprising the remaining gas constituents. In a desorption stage, the $C_4$ hydrocarbons are released again from the absorbent.

Inert absorbents used in the absorption stage are generally high-boiling nonpolar solvents in which the $C_4$ hydrocarbon mixture to be removed has a distinctly higher solubility than the remaining gas constituents. The absorption may be effected by simply passing the product gas stream c through the absorbent. However, it may also be effected in columns or in rotary absorbers. It is possible to work in cocurrent, countercurrent or crosscurrent. Examples of suitable absorption columns include tray columns having bubble-cap, centrifugal and/or sieve trays, columns having structured packings, for example sheet metal packings having a specific surface area of from 100 to 1000 $m^2/m^3$ such as Mellapak® 250 Y, and randomly packed columns. However, useful absorption columns also include trickle and spray towers, graphite block absorbers, surface absorbers such as thick-film and thin-film absorbers and also rotary columns, plate scrubbers, cross-spray scrubbers and rotary scrubbers.

Suitable absorbents are comparatively nonpolar organic solvents, for example aliphatic $C_5$- to $C_{18}$-alkenes, or aromatic hydrocarbons such as the middle oil fractions from paraffin distillation naphtha, or ethers having bulky groups, or mixtures of these solvents, to each of which a polar solvent such as dimethyl 1,2-phthalate may be added. Further suitable absorbents include esters of benzoic acid and phthalic acid with straight-chain $C_1$-$C_8$-alkanols, such as n-butyl benzoate, methyl benzoate, ethyl benzoate, dimethyl phthalate, diethyl phthalate, and also heat carrier oils, such as biphenyl and diphenyl ether, their chlorine derivatives and also triarylalkenes. A useful absorbent is a mixture of biphenyl and diphenyl ether, preferably in the azeotropic composition, for example the commercially available Diphyl®. Frequently, this solvent mixture contains dimethyl phthalate in an amount of 0.1 to 25% by weight. Further suitable absorbents are pentanes, hexanes, heptanes, octanes, nonanes, decanes, unidecanes, dodecanes, tridecanes, tetradecanes, pentadecanes, hexadecanes, heptadecanes and octadecanes, or fractions obtained from refinery streams which have the linear alkanes mentioned as main components. Further suitable absorbents are butyrolactone, nitrites such as acetonitrile, propionitrile, methoxypropionitrile, ketones such as acetone, furfural, N-alkyl-substituted lower aliphatic amides such as dimethylformamide, diethylformamide, dimethylacetamide, diethylacetamide, N-formylmorpholine, N-alkyl-substituted cyclic amides (lactams) such as N-alkylpyrrolidones, especially N-methylpyrrolidone (NMP).

To desorb the $C_4$ hydrocarbons, the laden absorbent is heated and/or decompressed to a lower pressure, Alternatively, desorption may also be effected by stripping or in a combination of decompression, heating and stripping in one or more process steps. The absorbent regenerated in the desorption stage is recycled into the absorption stage.

In one process variant, the desorption step is carried out by decompressing and/or heating the laden desorbent.

In a preferred variant, the desorption is carried out in two stages, and the desorption is effected in the first stage exclusively by decompression and heating. The absorbent which, after this first stage, still has a significant residual loading of $C_4$ hydrocarbons is subjected to a second desorption stage in which combination of decompression and heating and stripping removes the residual $C_4$ hydrocarbons. Suitable gases for stripping are steam, air, nitrogen, carbon oxides or flue gases. When stripping with stream, the desorption is followed by a phase separation, in which an aqueous phase and an organic absorbent phase are obtained. The aqueous phase can be evaporated again and the stream used again as stripping medium. The regenerated absorbent from the second desorption stage is fed back to the absorption stage The offgas of the second desorption stage may be recycled into the first or second dehydrogenation stage.

The removal D is generally not entirely complete, so that, depending on the type of removal, small amounts or even only traces of the further gas constituents, especially of the low-boiling hydrocarbons, may be present in the $C_4$ product gas stream.

The volume flow reduction brought about by the removal D also deburdens the downstream process steps.

The offgas comprising the remaining gas constituents, which also still comprises oxygen, may be used, for example, to regenerate the catalyst bed in the first or second dehydrogenation zone.

The $C_4$ product gas stream d consisting substantially of n-butane, 2-butene and butadiene comprises generally from 20 to 80% by volume of butadiene, from 20 to 80% by volume of n-butane, from 0 to 50% by volume of 2-butene and from 0 to 20% by volume of 1-butene.

The product gas stream c or d may also comprise small amounts of oxygen. When the product gas stream c or d contains more than just minor traces of oxygen, a process stage is generally carried out to remove residual oxygen from the product gas stream c or d. The residual oxygen may have a troublesome effect insofar as it can act as an initiator for polymerization reactions in downstream process steps. This is a risk especially in the course of the distillative removal of butadiene (step E)) and can lead there to deposits of polymers (formation of "popcorn") in the extractive distillation column. Preference is given to carrying out the oxygen removal immediately after the oxidative dehydrogenation. To this end, a catalytic combustion stage is generally carried out in which oxygen is reacted with the hydrogen present in gas stream c, c' or d in the presence of a catalyst. This achieves a reduction in the oxygen content down to small traces. When the residual oxygen removal is carried out only after the absorption/desorption stage, i.e. only in gas stream d, hydrogen has to be added to gas stream d.

A suitable catalyst for the oxidation of hydrogen comprises, supported on α-alumina, from 0.01 to 0.1% by weight of platinum and from 0.01 to 0.1% by weight of tin, based on the total weight of the catalyst. Platinum and tin are used advantageously in a weight ratio of from 1:4 to 1:0.2, preferably in a ratio of from 1:2 to 1:0.5, in particular in a ratio of approximately 1:1. Advantageously, the catalyst comprises from 0.05 to 0.09% by weight of platinum and from 0.05 to 0.09% by weight of tin, based on the total weight of the catalyst. In addition to platinum and tin, alkali metal and/or alkaline earth metal compounds may if appropriate be used in amounts of less than 2% by weight, in particular less than 0.5% by weight. More preferably, the alumina catalyst comprises exclusively platinum and tin. The catalyst support of α-alumina advantageously has a BET surface area of from 0.5 to 15 $m^2/g$, preferably from 2 to 14 $m^2/g$, in particular from 7 to 11 $m^2/g$. The support used is preferably a shaped body. Preferred geometries are, for example, tablets, annular tablets, spheres, cylinders, star extrudates or toothed wheel-shaped extrudates having diameters of from 1 to 10 mm, preferably from 2 to 6 mm. Particular preference is given to spheres or cylinders, in particular cylinders.

Alternative processes for removing residual oxygen from the product gas stream c, c' or d comprise the contacting of the product gas stream with a mixture of metal oxides which comprise copper in reduced form in the 0 oxidation state. In addition, such a mixture generally also comprises aluminum oxides and zinc oxides, the copper content being typically up to 10% by weight. In this way, virtually full removal of residual oxygen is possible. In addition, further methods of removing oxygen traces may be used. Examples are the removal by means of molecular sieves, use of membranes or contacting with a $NaNO_2$ solution.

In one process step, E, the $C_4$ product gas stream d is separated by means of extractive distillation into a stream e1 consisting substantially of n-butane and 2-butene, and a product-of-value stream e2 consisting substantially of butadiene.

The stream e1 consisting substantially of n-butane and 2-butene is recycled at least partly into the first dehydrogenation stage.

The extractive distillation may be carried out as described in Erdöl und Kohle-Erdgas-Petrochemie [Mineral Oil and Coal-Natural Gas-Petrochemistry] volume 34 (8), pages 343-346 or Ullmanns Enzyklopädie der Technischen Chemie, volume 9, 4th edition 1975, pages 1 to 18.

To this end, the $C_4$ product gas stream d is contacted in an extraction zone with an extractant, preferably an N-methylpyrrolidone (NMP)/water mixture. The extraction zone is generally configured in the form of a wash column which comprises trays, random packings or structured packings as internals. It generally has from 30 to 70 theoretical plates, so that sufficiently good separating action is achieved. The wash column preferably has a backwash zone in the top of the column. This backwash zone serves to recycle the extractant present in the gas phase by means of a liquid hydrocarbon reflux, for which the top fraction is condensed beforehand. As liquid hydrocarbon reflux, fresh buten to be added to the process can be used. Typical temperatures at the top of the column are between 30 and 60° C. The mass ratio of extractant to $C_4$ product gas stream d in the feed of the extraction zone is generally from 10:1 to 20:1.

Suitable extractants are butyrolactone, nitrites such as acetonitrile, propionitrile, methoxypropionitrile, ketones such as acetone, furfural, N-alkyl-substituted lower aliphatic amides such as dimethylformamide, diethylformamide, dimethylacetamide, diethylacetamide, N-formylmorpholine, N-alkyl-substituted cyclic amides (lactams) such as N-alkylpyrrolidones, especially N-methylpyrrolidone (NMP). In general, alkyl-substituted lower aliphatic amides or N-alkyl-substituted cyclic amides are used. Particularly advantageous are dimethylformamide, acetonitrile, furfural and especially NMP.

However, it is also possible to use mixtures of these extractants with one another, for example of NMP and acetonitrile, mixtures of these extractants with cosolvents and/or tert-butyl ethers, e.g. methyl tert-butyl ether, ethyl tert-butyl ether, propyl tert-butyl ether, n- or isobutyl tert-butyl ether. Particularly suitable is NMP, preferably in aqueous solution, preferably with from 0 to 20% by weight of water, more preferably with from 7 to 10% by weight of water, in particular with 8.3% by weight of water.

In the extractive distillation column, a gaseous stream e1 consisting substantially of n-butane and 2-butene is obtained and is generally drawn off via the top of the column, and the side draw stream obtained is a mixture of extractant and butadiene. From this mixture, butadiene may be obtained subsequently as a pure product. The extractant which also comprises butadiene and any secondary components (impurities) is obtained as a bottom draw stream. The bottom draw stream is, if appropriate after carrying out further purification steps, recycled back into the extractive distillation.

In general, the stream e1 consisting substantially of n-butane and 2-butene comprises from 50 to 100% by volume of n-butane, from 0 to 50% by volume of 2-butene and from 0 to 3% by volume of further constituents such as isobutane, isobutene, propane, propene and $C_5^+$ hydrocarbons. Stream e1 is recycled at least partly into the first dehydrogenation stage.

For example, the extractive distillation, isolation of the pure butadiene and purification of the extractant may be carried out as follows: the side draw stream of the extractive distillation column, composed of extractant and butadiene which still comprises impurities (acetylene, propyne, 1,2-butadiene), is fed into a wash column which is charged with fresh extractant. At the top of the wash column, crude butadiene which comprises, for example, 98% by weight of butadiene is drawn off. The bottom draw stream is enriched with acetylene and is recycled into the extractive distillation. The crude butadiene may comprise propyne and 1,2-butadiene as impurities. To remove these impurities, the crude butadiene is fed to a first purifying distillation column and a propyne-enriched butadiene stream is removed overhead. The bottom draw stream which is substantially propyne-free, but still comprises traces of 1,2-butadiene, is fed into a second purifying distillation column in which a substantially 1,2-butadiene-free pure butadiene stream having a purity of, for example, at least 99.6% by weight as a top draw stream or side draw stream in the rectifying section of the column, and a 1,2-butadiene-enriched bottom draw stream, are obtained.

To purify the extractant, the extractant is party or completely discharged from the extractive distillation column as a bottom draw stream and regenerated as follows: the extraction solution is transferred into a desorption zone with reduced pressure and/or elevated temperature compared to the extraction zone, and butadiene and acetylene traces present are desorbed from the extraction solution. The desorption zone may be designed, for example, in the form of a wash column which has from 5 to 15, preferably from 8 to 10, theoretical plates and a backwash zone having, for example, 4 theoretical plates. This backwash zone serves to recover the extractant present in the gas phase by means of liquid hydrocarbon reflux, for which the top fraction is condensed beforehand, or by means of water addition. The internals provided are structured packings, trays or random packings. The pressure at the top of the column is, for example, 1.5 bar. The temperature in the bottom of the column is, for example, from 130 to 150° C. At the bottom of the column, a substantially acetylene-free extractant is obtained and is recycled into the extractive distillation column. The top draw stream of the wash column is recycled to the bottom of the extractive distillation column. The bottom draw stream of the wash column is recycled to the top of the extractive distillation column. Alternatively, the desorption zone can be operated at the same pressure as the extractive distillation.

The product-of-value stream e2, as is obtained, for example, as the top draw stream of the second purifying distillation column, may comprise up to 100% by volume of butadiene.

BRIEF DESCRIPTION OF THE DRAWING

FIG. 1 depicts the process of the following example, which is an embodiment of the present invention The invention is illustrated in detail by the example which follows.

EXAMPLE

A feed gas stream (4) comprising n-butane, said stream being obtained by combining a fresh gas stream (1) and a recycle stream (15), is fed to the first, autothermally operated, nonoxidative catalytic n-butane dehydrogenation stage (BDH) (20). To provide the heat required for the endothermic dehydrogenation, the hydrogen formed in the dehydrogenation is combusted selectively, for which combustion air is fed as stream (2). In order to counteract carbonization of the catalyst and prolong the lifetime of the catalyst, steam (3) is also added. A dehydrogenation gas mixture (5) is obtained, which is cooled after leaving the nonoxidative n-butane dehydrogenation stage (20) and fed to the second, oxidative, n-butane dehydrogenation stage (ODH) (21). Also fed to the ODH is an air stream (6). For BDH and ODH, based on experimental results, the degrees of conversion and selectivities reproduced in Table 1 were assumed.

TABLE 1

| Reaction stage | Conversion [%] | Selectivity [%] |
|---|---|---|
| Autothermal dehydrogenation (BDH) | 50.9 (n-butane) | 97.9 (to butenes/butadiene) |
| Oxidative dehydrogenation (ODH) | 100.0 (1-butene) 92.7 (2-butene) | 95.0 (to butadiene) |

The exit gas (7) of the ODH is compressed in two stages with intermediate cooling. The aqueous condensate (8) obtained in the intermediate coolings is discharged from the process. From the aqueous condensate (8), an organic phase comprising $C_4$ hydrocarbons may be removed and fed back to the first dehydrogenation stage. The compressed, butadiene-containing gas (9) is fed to an absorption stage (23) which is operated with tetradecane as the absorbent. In the absorption stage, an absorbent stream (11) laden with the $C_4$ hydrocarbons and an inert gas stream (10) which is discharged from the process are obtained. From the laden absorbent (11), a stream (13) comprising butadiene, n-butane and 2-butene is removed in the desorption column (24), and the absorbent (12) is recovered. This is stripped with air (18) in a stripping column (25) in order to remove traces of $C_4$ hydrocarbons. The gaseous top draw stream (19) of the stripping column (25), which consists of air and $C_4$ hydrocarbons, is fed to the ODH (21). The stream (17) of the regenerated absorbent is supplemented by fresh absorbent (17a) and recycled into the absorption stage (23). Stream (13) is compressed and fed to a reactor (26) in which residual oxygen remaining in stream (13) is reacted with hydrogen (13a) catalytically to give water. The substantially oxygen-free $C_4$ hydrocarbon stream (14) is separated in an extractive distillation stage (27) using aqueous N-methyl-pyrrolidone solution into a butadiene-containing product stream (16) and an n-butane-containing recycle stream (15) which is recycled into the BDH.

The results of the simulation are shown in Table 2. The composition of the streams (1) to (19) is reported in parts by weight.

TABLE

| | Stream | | | | | | | | |
|---|---|---|---|---|---|---|---|---|---|
| | 1 | 2 | 3 | 4 | 5 | 6 | 7 | 8 | 9 |
| Amount [kg/h] | 24425 | 20937 | 1203 | 72269 | 72268 | 33401 | 135555 | 14428 | 121127 |
| PROPANE | 0.0000 | 0.0000 | 0.0000 | 0.0063 | 0.0117 | 0.0000 | 0.0063 | 0.0037 | 0.0066 |
| PROPENE | 0.0000 | 0.0000 | 0.0000 | 0.0000 | 0.0000 | 0.0000 | 0.0000 | 0.0000 | 0.0000 |
| BUTANE | 1.0000 | 0.0000 | 0.0000 | 0.6716 | 0.3340 | 0.0000 | 0.2261 | 0.0045 | 0.2525 |
| ISOBUTANE | 0.0000 | 0.0000 | 0.0000 | 0.0000 | 0.0000 | 0.0000 | 0.0000 | 0.0000 | 0.0000 |
| 1-BUTENE | 0.0000 | 0.0000 | 0.0000 | 0.0000 | 0.0930 | 0.0000 | 0.0000 | 0.0000 | 0.0000 |
| CIS-2-BUTENE | 0.0000 | 0.0000 | 0.0000 | 0.0029 | 0.0963 | 0.0000 | 0.0026 | 0.0052 | 0.0023 |
| TRANS-2-BUTENE | 0.0000 | 0.0000 | 0.0000 | 0.0067 | 0.1210 | 0.0000 | 0.0058 | 0.0108 | 0.0052 |
| 1,3-BUTADIENE | 0.0000 | 0.0000 | 0.0000 | 0.0000 | 0.0176 | 0.0000 | 0.1858 | 0.0032 | 0.2076 |
| ISOBUTENE | 0.0000 | 0.0000 | 0.0000 | 0.0000 | 0.0000 | 0.0000 | 0.0000 | 0.0000 | 0.0000 |
| WATER | 0.0000 | 0.0000 | 1.0000 | 0.0184 | 0.0864 | 0.0000 | 0.1047 | 0.9663 | 0.0020 |
| TETRADECANE | 0.0000 | 0.0000 | 0.0000 | 0.0000 | 0.0000 | 0.0000 | 0.0003 | 0.0031 | 0.0000 |
| 1,2-BUTADIENE | 0.0000 | 0.0000 | 0.0000 | 0.0000 | 0.0000 | 0.0000 | 0.0000 | 0.0000 | 0.0000 |
| CARBON DIOXIDE | 0.0000 | 0.0000 | 0.0000 | 0.0040 | 0.0094 | 0.0000 | 0.0299 | 0.0029 | 0.0331 |
| HYDROGEN | 0.0000 | 0.0000 | 0.0000 | 0.0000 | 0.0048 | 0.0000 | 0.0025 | 0.0000 | 0.0028 |
| OXYGEN | 0.0000 | 0.2329 | 0.0000 | 0.0644 | 0.0001 | 0.2329 | 0.0197 | 0.0001 | 0.0221 |
| $N_2$ | 0.0000 | 0.7671 | 0.0000 | 0.2257 | 0.2257 | 0.7671 | 0.4162 | 0.0003 | 0.4658 |
| Temperature [° C.] | 25.0 | 143.2 | 143.6 | 420.0 | 590.0 | 143.2 | 380.0 | 30.0 | 30.0 |
| Pressure [bar] | 5.0 | 3.2 | 4.0 | 3.2 | 2.7 | 2.7 | 2.4 | 10.3 | 10.3 |

| | Stream | | | | | | |
|---|---|---|---|---|---|---|---|
| | 10 | 11 | 12 | 13 | 13a | 14 | 15 |
| Amount [kg/h] | 63626 | 338501 | 291984 | 46772 | 1 | 46668 | 25708 |
| PROPANE | 0.0053 | 0.0014 | 0.0000 | 0.0098 | 0.0000 | 0.0098 | 0.0178 |
| PROPENE | 0.0000 | 0.0000 | 0.0000 | 0.0000 | 0.0000 | 0.0000 | 0.0000 |
| BUTANE | 0.0004 | 0.0905 | 0.0225 | 0.5158 | 0.0000 | 0.5167 | 0.9379 |
| ISOBUTANE | 0.0000 | 0.0000 | 0.0000 | 0.0000 | 0.0000 | 0.0000 | 0.0000 |
| 1-BUTENE | 0.0000 | 0.0000 | 0.0000 | 0.0000 | 0.0000 | 0.0000 | 0.0000 |
| CIS-2-BUTENE | 0.0000 | 0.0008 | 0.0002 | 0.0045 | 0.0000 | 0.0045 | 0.0081 |
| TRANS-2-BUTENE | 0.0000 | 0.0019 | 0.0005 | 0.0103 | 0.0000 | 0.0103 | 0.0188 |
| 1,3-BUTADIENE | 0.0001 | 0.0743 | 0.0145 | 0.4484 | 0.0000 | 0.4491 | 0.0000 |
| ISOBUTENE | 0.0000 | 0.0000 | 0.0000 | 0.0000 | 0.0000 | 0.0000 | 0.0000 |
| WATER | 0.0020 | 0.0004 | 0.0000 | 0.0026 | 0.0000 | 0.0028 | 0.0050 |
| TETRADECANE | 0.0000 | 0.8299 | 0.9622 | 0.0018 | 0.0000 | 0.0001 | 0.0002 |
| 1,2-BUTADIENE | 0.0000 | 0.0000 | 0.0000 | 0.0000 | 0.0000 | 0.0000 | 0.0000 |
| CARBON DIOXIDE | 0.0585 | 0.0009 | 0.0000 | 0.0062 | 0.0000 | 0.0062 | 0.0112 |
| HYDROGEN | 0.0054 | 0.0000 | 0.0000 | 0.0000 | 1.0000 | 0.0000 | 0.0000 |
| OXYGEN | 0.0420 | 0.0000 | 0.0000 | 0.0002 | 0.0000 | 0.0000 | 0.0000 |
| $N_2$ | 0.8864 | 0.0001 | 0.0000 | 0.0005 | 0.0000 | 0.0005 | 0.0010 |
| Temperature [° C.] | 28.3 | 53.3 | 122.5 | 86.0 | 25.0 | 201.1 | 120.3 |
| Pressure [bar] | 10.3 | 10.3 | 3.0 | 3.0 | 5.0 | 5.0 | 5.0 |

TABLE-continued

|  | Stream | | | | |
| --- | --- | --- | --- | --- | --- |
|  | 16 | 17a | 17 | 18 | 19 |
| Amount [kg/h] | 20960 | 7 | 280993 | 18895 | 29886 |
| PROPANE | 0.0000 | 0.0000 | 0.0000 | 0.0000 | 0.0004 |
| PROPENE | 0.0000 | 0.0000 | 0.0000 | 0.0000 | 0.0000 |
| BUTANE | 0.0000 | 0.0000 | 0.0002 | 0.0000 | 0.2179 |
| ISOBUTANE | 0.0000 | 0.0000 | 0.0000 | 0.0000 | 0.0000 |
| 1-BUTENE | 0.0000 | 0.0000 | 0.0000 | 0.0000 | 0.0000 |
| CIS-2-BUTENE | 0.0000 | 0.0000 | 0.0000 | 0.0000 | 0.0023 |
| TRANS-2-BUTENE | 0.0000 | 0.0000 | 0.0000 | 0.0000 | 0.0048 |
| 1,3-BUTADIENE | 1.0000 | 0.0000 | 0.0000 | 0.0000 | 0.1412 |
| ISOBUTENE | 0.0000 | 0.0000 | 0.0000 | 0.0000 | 0.0000 |
| WATER | 0.0000 | 0.0000 | 0.0000 | 0.0000 | 0.0000 |
| TETRADECANE | 0.0000 | 1.0000 | 0.9997 | 0.0000 | 0.0014 |
| 1,2-BUTADIENE | 0.0000 | 0.0000 | 0.0000 | 0.0000 | 0.0000 |
| CARBON DIOXIDE | 0.0000 | 0.0000 | 0.0000 | 0.0000 | 0.0000 |
| HYDROGEN | 0.0000 | 0.0000 | 0.0000 | 0.0000 | 0.0000 |
| OXYGEN | 0.0000 | 0.0000 | 0.0000 | 0.2330 | 0.1471 |
| $N_2$ | 0.0000 | 0.0000 | 0.0000 | 0.7670 | 0.4848 |
| Temperature [° C.] | 120.3 | 30.0 | 69.3 | 120.0 | 70.7 |
| Pressure [bar] | 5.0 | 10.3 | 2.8 | 2.8 | 2.8 |

What is claimed is:

1. A process for preparing butadiene from n-butane, comprising

A) providing a feed gas stream (a) comprising n-butane;

B) feeding said feed gas stream (a) into at least one first dehydrogenation zone and nonoxidatively catalytically dehydrogenating n-butane to obtain a product gas stream (b) comprising n-butane, 1-butene, 2-butene, butadiene, hydrogen, and low-boiling secondary constituents, and optionally comprising carbon oxides and/or steam;

C) feeding said product gas stream (b) and an oxygenous gas into at least one second dehydrogenation zone and oxidatively dehydrogenating n-butane, 1-butene and 2-butene to obtain a product gas stream (c) comprising n-butane, 2-butene, butadiene, low-boiling secondary constituents, carbon oxides, and steam, said product gas stream (c) having a higher content of butadiene than product gas stream (b);

D) removing said low-boiling secondary constituents and steam from said product gas stream (c) to obtain a $C_4$ product gas stream (d) substantially comprising n-butane, 2-butene and butadiene;

E) separating by extractive distillation said $C_4$ product gas stream (d) into a stream (e1) substantially comprising n-butane and 2-butene and a product-of-value stream (e2) substantially comprising butadiene;

F) recycling said stream (e1) into said first dehydrogenation zone;

wherein at least a portion of the oxygen remaining in said product gas streams (c) and/or (d) after C) or D) is removed by reacting it catalytically with hydrogen.

2. The process according to claim 1, wherein said oxidative dehydrogenation of C) is carried out autothermally while feeding in said oxygenous gas.

3. The process according to claim 2, wherein said oxygenous gas is air.

4. The process according to claim 1, wherein said feed stream (a) is obtained from liquefied petroleum gas.

5. The process according to claim 1, wherein in D) said steam is removed by cooling and/or decompressing product gas stream (c) in one or more cooling and/or evaporation stages to obtain a low-water product gas stream (c').

6. The process according to claim 5, wherein in D) said low-water product gas stream (c') is contacted with an inert absorbent to obtain an inert absorbent laden with $C_4$ hydrocarbons and an offgas comprising the remaining gas constituents of said low-water product gas stream (c'), wherein said $C_4$ hydrocarbons are released from said inert absorbent in a subsequent desorption stage.

7. The process according to claim 1, wherein said extractive distillation in E) is carried out using an N-methylpyrrolidone/water mixture as an extractant.

* * * * *